(12) United States Patent
Somasundaram et al.

(10) Patent No.: US 9,626,462 B2
(45) Date of Patent: Apr. 18, 2017

(54) DETECTING TOOTH WEAR USING INTRA-ORAL 3D SCANS

(71) Applicant: 3M INNOVATIVE PROPERTIES COMPANY, St. Paul, MN (US)

(72) Inventors: Guruprasad Somasundaram, Minneapolis, MN (US); Evan J. Ribnick, St. Louis Park, MN (US); Ravishankar Sivalingam, Woodbury, MN (US); Aya Eid, St. Paul, MN (US); Theresa M. Meyer, Osceola, WI (US); Golshan Golnari, Minneapolis, MN (US); Anthony J. Sabelli, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 180 days.

(21) Appl. No.: 14/321,318

(22) Filed: Jul. 1, 2014

(65) Prior Publication Data

US 2016/0004811 A1 Jan. 7, 2016

(51) Int. Cl.
*G06K 9/34* (2006.01)
*G06F 17/50* (2006.01)

(52) U.S. Cl.
CPC .................................. *G06F 17/50* (2013.01)

(58) Field of Classification Search
None
See application file for complete search history.

(56) References Cited

U.S. PATENT DOCUMENTS

| | | | |
|---|---|---|---|
| 6,726,478 B1 * | 4/2004 | Isiderio | A61C 7/00 433/213 |
| 7,063,532 B1 * | 6/2006 | Jones | A61C 7/00 433/213 |
| 7,077,647 B2 | 7/2006 | Choi | |
| 7,442,041 B2 | 10/2008 | Imgrund | |
| 7,471,821 B2 | 12/2008 | Rubbert | |
| 7,605,817 B2 | 10/2009 | Zhang | |
| 7,695,278 B2 | 4/2010 | Sporbert | |
| 7,826,646 B2 | 11/2010 | Pavlovskaia | |
| 7,956,862 B2 | 6/2011 | Zhang | |
| 8,075,306 B2 | 12/2011 | Kitching | |

(Continued)

OTHER PUBLICATIONS 3D surface imaging—at., British dental journal, Ireland et al., 2008, pp. 387-392.*

(Continued)

*Primary Examiner* — Jayesh A Patel

(57) ABSTRACT

A method for detecting tooth wear using digital 3D models of teeth taken at different times. The digital 3D models of teeth are segmented to identify individual teeth within the digital 3D model. The segmentation includes performing a first segmentation method that over segments at least some of the teeth within the model and a second segmentation method that classifies points within the model as being either on an interior of a tooth or on a boundary between teeth. The results of the first and second segmentation methods are combined to generate segmented digital 3D models. The segmented digital 3D models of teeth are compared to detect tooth wear by determining differences between the segmented models, where the differences relate to the same tooth to detect wear on the tooth over time.

22 Claims, 9 Drawing Sheets

(56) References Cited

U.S. PATENT DOCUMENTS

| | | | |
|---|---|---|---|
| 8,244,028 B2 | 8/2012 | Kuo | |
| 8,275,180 B2 | 9/2012 | Kuo | |
| 8,457,772 B2* | 6/2013 | Giasson | A61C 13/0004 433/167 |
| 8,591,225 B2* | 11/2013 | Wu | A61C 7/00 382/128 |
| 8,897,902 B2* | 11/2014 | See | A61C 7/002 433/201.1 |
| 2002/0037489 A1* | 3/2002 | Jones | A61C 7/00 433/24 |
| 2002/0150859 A1* | 10/2002 | Imgrund | A61C 7/00 433/24 |
| 2003/0224316 A1* | 12/2003 | Marshall | A61C 7/146 433/24 |
| 2004/0152036 A1* | 8/2004 | Abolfathi | A61C 7/00 433/24 |
| 2005/0095562 A1 | 5/2005 | Sporbert et al. | |
| 2007/0024611 A1 | 2/2007 | Ingram | |
| 2008/0020350 A1* | 1/2008 | Matov | G06T 17/20 433/213 |
| 2008/0136820 A1 | 6/2008 | Yang et al. | |
| 2008/0154419 A1* | 6/2008 | Cheng | A61C 7/00 700/118 |
| 2010/0068672 A1* | 3/2010 | Arjomand | A61C 7/00 433/24 |
| 2010/0151404 A1* | 6/2010 | Wu | A61C 7/00 433/24 |
| 2011/0104630 A1* | 5/2011 | Matov | A61C 7/00 433/24 |
| 2013/0022255 A1 | 1/2013 | Chen et al. | |
| 2013/0336563 A1 | 12/2013 | Wilson et al. | |
| 2014/0003718 A1 | 1/2014 | Eid et al. | |

OTHER PUBLICATIONS

"3M True Definition Scanner" [on line], [retrieved from the internet on Sep. 11, 2014], URL <http://solutions.3m.com/wps/portal/3M/en_US/3M-ESPE-NA/dental-professionals/products/category/digital-materials/true-definition-scanner/>, pp. 1-2.

"Bruxism", Wikipedia, the free encyclopedia, [on line], [retrieved from internet on Sep. 15, 2014], URL: <http://en.wikipedia.org/wiki/Bruxism>, pp. 1.

"Triangle mesh", Wikipedia, the free encyclopedia, [on line], [retrieved from internet on Sep. 15, 2014], URL:<http://en.wikipedia.org/wiki/Triangle_mesh>, pp. 1-2.

"Unitek TMP Digital Models" [on line], [retrieved on Sep. 9, 2014], URL: <http://solutions.3m.com/wps/portal/3M/en_US/orthodontics/Unitek/products/digital/ttm/Digital-Models/>, pp. 1.

Belongie, "Shape Matching and Object Recognition Using Shape Contexts", IEEE Transaction Pattern Analysis and Machine Intelligence, 2002, vol. 24, No. 4, pp. 509-522.

Chang, "LIBSVM: a library for support vector machines", ACM Transactions on Intelligent Systems and Technology, Apr. 2011, No. 3, Article 27, pp. 27:1-27:27.

Cortes, "Support-Vector Networks", Machine Learning, 1995, vol. 20, pp. 273-297.

Drucker; "Support Vector Regression Machines", Neural Information Processing Systems 9, MIT Press, 1997, pp. 155-161.

Galar, "A Review on Ensembles for the Class Imbalance Problem: Bagging-, Boosting-, and Hybrid-Based Approaches", IEEE Transactions on Systems, Man, and Cybernetics, Part C: Applications and Reviews, Jul. 2012, vol. 42, No. 4, pp. 463-484.

Hilaga, "Topology Matching for Fully Automatic Similarity Estimation of 3D Shapes", Proceedings of the 28th Annual Conference on Computer Graphics and Interactive Techniques, 2001, pp. 203-212.

Johnson, "Using Spin Images for Efficient Object Recognition in Cluttered 3D Scenes", IEEE Transaction on Pattern Analysis and Machine Intelligence, 1999, vol. 21, No. 5, pp. 433-449.

Kalogerakis, "Learning 3D mesh segmentation and labeling", ACM Transactions on Graphics, 2010, pp. 1-13.

Kondo, "Tooth Segmentation of Dental Study Models Using Range Images", IEEE Transactions on Medical Imaging, 2004, vol. 23, No. 3, pp. 350-362.

Koyano, "Assessment of bruxism in the clinic", Journal of Oral Rehabilitation, Jul. 2008, vol. 35, pp. 495-508.

Kumar, "Improved Segmentation of Teeth in Dental Models", computer-Aided Design & Applications, 2011, vol. 8, No. 2, pp. 211-224.

Lafferty, "Conditional Random Fields: Probabilistic Models for Segmenting and Labeling Sequence Data", Proceedings of the Eighteenth International Conference on Machine Learning, 2001, pp. 282-289.

Lazebnik, "Beyond Bags of Features: Spatial Pyramid Matching for Recognizing Natural Scene Categories", IEEE Conference on Computer Vision and Pattern Recognition, 2006, pp. 2169-2178.

Liu, "A Part-aware Surface Metric for Shape Analysis", Computer Graphics Forum, Blackwell Publishing Ltd, 2009, vol. 28. No. 2, pp. 397-406.

Marbach, "Reliability of clinician judgments of bruxism", Journal of Oral Rehabilitation, 2003, vol. 30, pp. 113-118.

Quinlan, "Induction of Decision Trees", Machine Learning 1, 1986, pp. 81-106.

Rusinkiewicz, "Efficient Variants of the ICP Algorithm", IEEE International Conference on 3-D Digital Imaging and Modeling, 2001, pp. 1-8.

Russell, "Artificial Intelligence: A Modern Approach", 2nd ed., Upper Saddle River, New Jersey: Prentice Hall, pp. 111-114.

Seiffert, "RUSBoost: A Hybrid Approach to Alleviating Class Imbalance", IEEE Transactions on Systems, Man and Cybernetics, Part A: Systems and Humans, 2010, vol. 40, No. 1, pp. 185-197.

Shapira, Consistent mesh partitioning and skeletonisation using the shape diameter function, The Visual Computer, 2008. vol. 24, pp. 249-259.

Taubin, "Geometric Signal Processing on Polygonal Meshes", Eurogrphics State of the Art Report, 2000, pp. 1-11.

PCT International Search Report for PCT/US2015/037868, mailed Oct. 20, 2015.

* cited by examiner

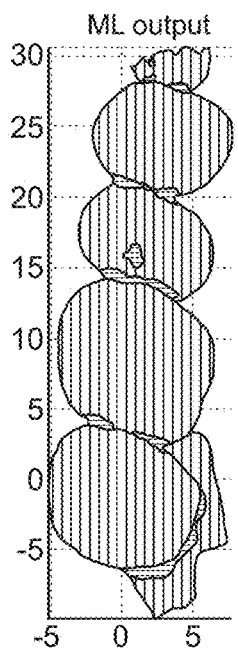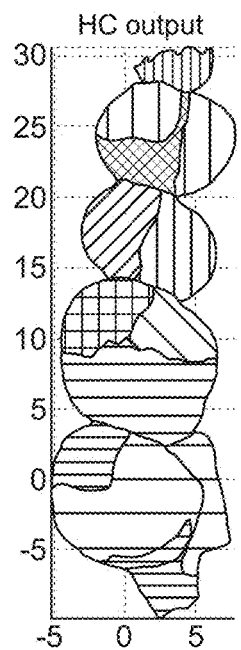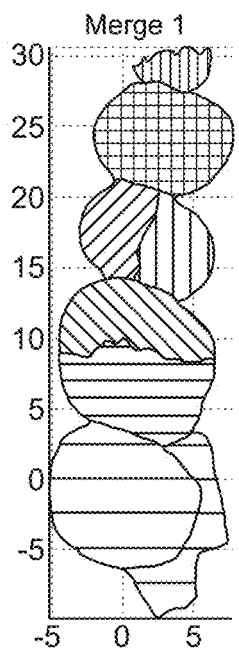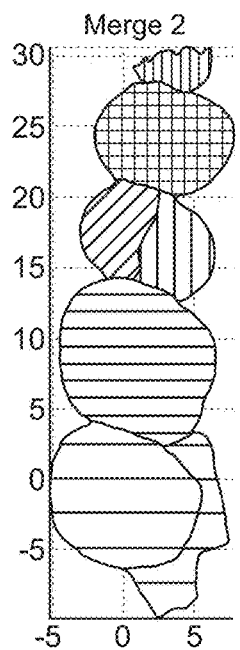
FIG. 9A   FIG. 9B   FIG. 9C   FIG. 9D
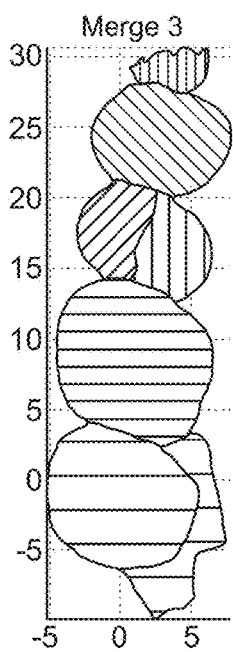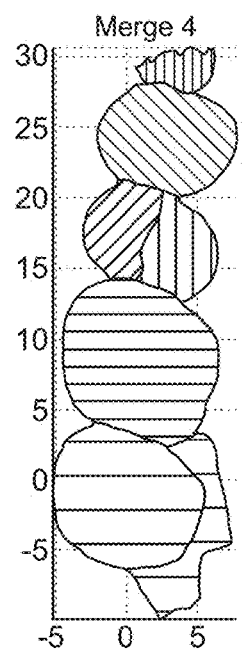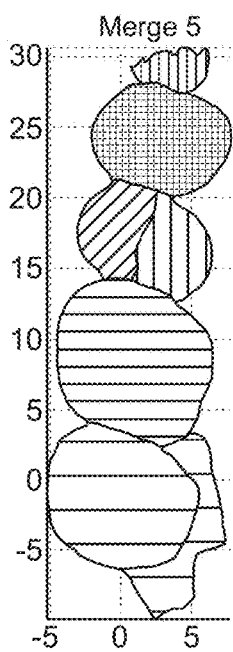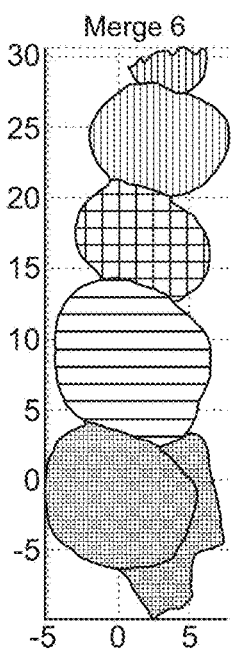
FIG. 9E   FIG. 9F   FIG. 9G   FIG. 9H

DETECTING TOOTH WEAR USING INTRA-ORAL 3D SCANS

BACKGROUND

Tooth wear (for example, associated with Bruxism) and gingival recession are both conditions (among other defects) that, if not treated in a timely manner by dental professionals, can have serious medical consequences. In the case of Bruxism, lateral movements and tooth grinding can cause significant tooth wear and lead to muscle pain, temporomandibular joint issues, and headaches. In some cases, this may lead to the dentin being exposed, dental decay, and even tooth fracture.

Despite the potential severity of these consequences, the tools available to dental professionals for diagnosing and assessing the severity of tooth wear and gingival recession are limited. In the case of tooth wear, these tools include patient questionnaires, clinical examination by a dentist, and bite force measurements. Clinical examinations may be performed using the Individual Tooth-Wear Index, which provides a rating between 0 and 3 based on visual assessment by a dentist. However, none of these techniques directly measure the amount of tooth wear exhibited, and most of them are subjective and qualitative. All of this suggests the need for a more quantitative, repeatable metric that can be used for the assessment of these conditions.

SUMMARY

A first method for detecting tooth wear, consistent with the present invention, includes receiving first and second digital 3D models of teeth, where the digital 3D models of teeth were taken at different times. The first digital 3D model of teeth is segmented to separate individual teeth within the first digital 3D model of teeth, and the segmenting step is repeated for the second digital 3D model of teeth to generate a segmented second digital 3D model of teeth. The segmented first digital 3D model of teeth are compared with the segmented second digital 3D model of teeth to detect tooth wear by determining differences between the segmented first digital 3D model of teeth and the segmented second digital 3D model of teeth, where the differences relate to a same tooth.

A second method for detecting tooth wear, consistent with the present invention, includes receiving first and second digital 3D models of teeth, where the digital 3D models of teeth were taken at different times. The first digital 3D model of teeth is segmented to separate individual teeth within the first digital 3D model of teeth, which includes performing a first segmentation method for the first digital 3D model of teeth and performing a second segmentation method, different from the first segmentation method, for the first digital 3D model of teeth. The segmenting step is repeated for the second digital 3D model of teeth to generate a segmented second digital 3D model of teeth. The segmented first digital 3D model of teeth are compared with the segmented second digital 3D model of teeth to detect tooth wear by determining differences between the segmented first digital 3D model of teeth and the segmented second digital 3D model of teeth, where the differences relate to a same tooth.

BRIEF DESCRIPTION OF THE DRAWINGS

The accompanying drawings are incorporated in and constitute a part of this specification and, together with the description, explain the advantages and principles of the invention. In the drawings.

FIGS. 9A-9H illustrate merging of the results of two different segmentation methods to segment teeth in a digital 3D model;

DETAILED DESCRIPTION

The use of digital 3D models in the dental market is becoming more prevalent. These models can be acquired in vivo using an intra-oral scanner or off-line by laser scanning of a traditional impression. The digital 3D models can be used for varied clinical tasks including treatment planning, crown and implant preparation, and in diagnostic aides, for example to assess tooth wear.

Figure 1:
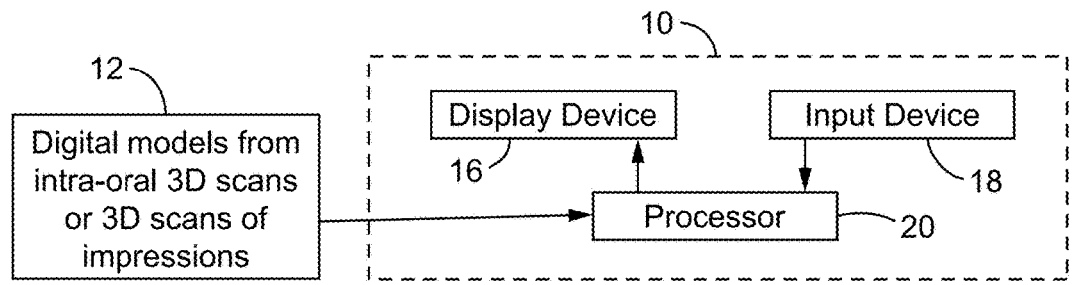
FIG. 1 is a diagram of a system for detecting tooth wear using a digital 3D model based upon intra-oral 3D scans or 3D scans from impressions.
Figure 2:
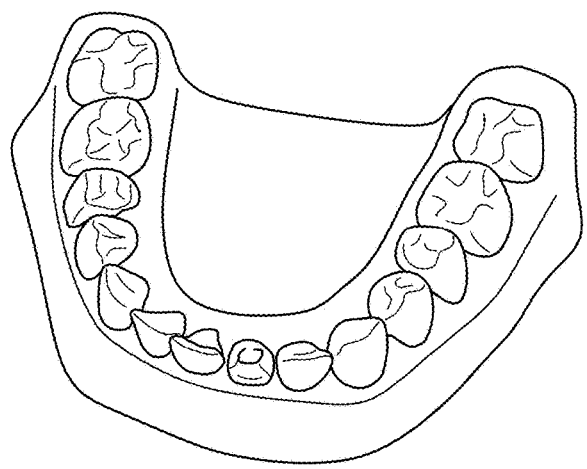
FIG. 2 illustrates a 3D model of teeth from intra-oral scans.

FIG. 1 is a diagram of a system 10 for detecting tooth wear using a digital 3D model based upon intra-oral 3D scans. System 10 includes a processor 20 receiving digital 3D models of teeth (12) from intra-oral 3D scans or scans of impressions of teeth. System 10 can also includes an electronic display device 16, such as a liquid crystal display (LCD) device, for displaying indications of tooth wear and an input device 18 for receiving user commands or other information. An example of digital 3D model of a patient's teeth from a scan is shown in FIG. 2. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth. System 10 can be implemented with, for example, a desktop, notebook, or tablet computer. System 10 can receive the 3D scans locally or remotely via a network.

For certain diagnostic tasks, the individual teeth in the model need to be segmented from one another before the desired analysis or manipulation can be performed. In some cases, a software interface may be presented in order for a user to perform this segmentation, or some parts of it, manually. However, this process can be quite labor intensive and tedious. As such, the automation of this task is desirable.

Figure 3:
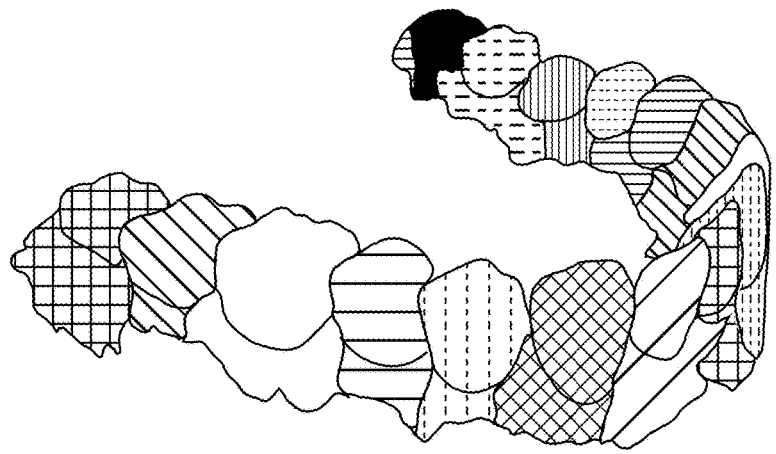
FIG. 3 illustrates a 3D model of teeth segmented to digitally separate each tooth.

An example of teeth that have been segmented in a digital model is shown in FIG. 3. The segmentation provides for separating individual teeth in the digital 3D model, as represented by the shading in FIG. 3, and each tooth in the model can essentially be digitally separated from the other teeth for further processing to detect tooth wear. Using a segmented digital 3D model for comparing or analyzing individual teeth is more accurate than comparing whole or partial arches within the model.

Described herein are techniques for tooth segmentation within a digital 3D model. The technique is a combination of two separate algorithms and combines the strengths of both of them. The first algorithm is a geometric hill-climbing approach which takes into account topological structures such as height and curvature. The second algorithm is a machine learning approach which classifies each point on the surface as belonging to either a boundary or a non-boundary. Alternatively, the second algorithm is interstice detection which classifies a set of planes (or points) that approximate the intersticial spaces between teeth. The second algorithm can be complementary to the first algorithm (geometric hill-climbing) and combined with the first algorithm to produce a resulting segmentation. As another alternative to the second algorithm, the first algorithm can be combined with user input estimating centroids of teeth in the digital 3D model. Instead of merging the results of two algorithms, only one algorithm can be used to segment the digital 3D model such as any one of the algorithms described herein.

The 3D scans addressed herein are represented as triangular meshes. The triangular mesh is common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Figure 4:
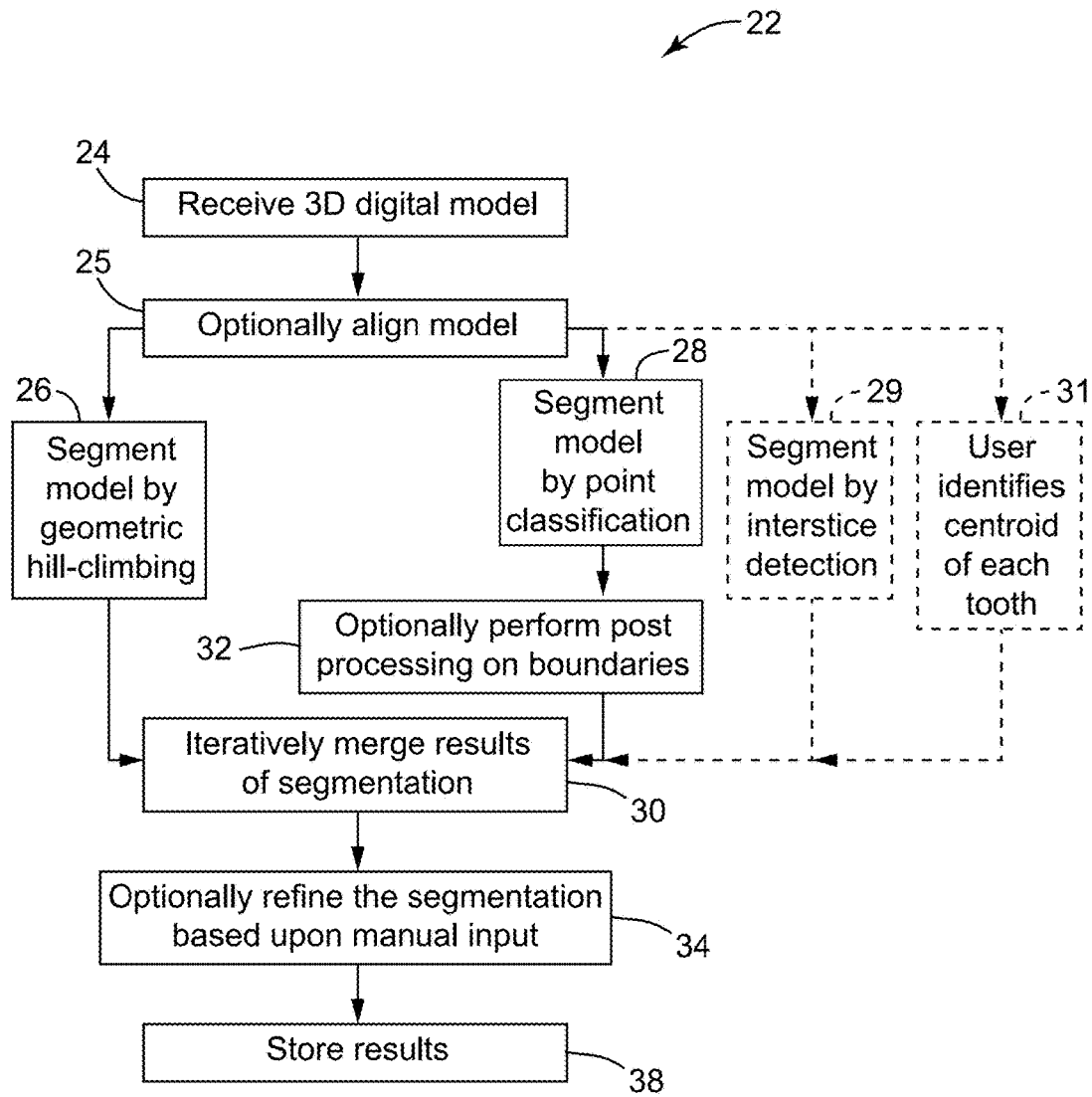
FIG. 4 is a flow chart of a method for segmenting teeth in a digital 3D model.

FIG. 4 is a flow chart of a method 22 for segmenting teeth in a digital 3D model. Method 22 can be implemented in software or firmware modules, for example, for execution by processor 20. Method 22 can alternatively be implemented in hardware modules or a combination of software and hardware.

Method 22 includes receiving a digital 3D model of a patient's teeth (step 24) and optionally aligning the model (step 25). Method 22 then involving segmenting the model by geometric hill-climbing (step 26) and point classification (step 28). Optionally, post processing on boundaries of the segmentation by point classification is performed (step 32). As an alternative to point classification, the model can be segmented by interstice detection (step 29). As another alternative to point classification, method 22 can receive user input identifying centroids of each tooth in the model (step 31).

The results of the segmentation methods are iteratively merged (step 30). In particular, the results of segmentation by hill-climbing are merged with the results of segmentation by point classification or interstice detection or user input identifying the centroids. The merged segmentation can optionally be refined based upon manual, for example user-entered, input (step 34). The results of the segmentation are stored (step 38). The segmentation results in a separate mesh for each tooth from the digital 3D model, as illustrated in FIG. 3. These steps are described in more detail below.

The optional alignment step 25 can be implemented using a Support Vector Regression (SVR) method to find the occlusal plane fitted to a mesh of the teeth in the digital 3D model. The alignment can be used to have the teeth in the digital 3D model essentially aligned with the Y axis.

The alignment can use the LIBSVM toolbox and $\epsilon$–SVR method. The kernel is chosen to be linear and $\epsilon=5$. The training is based on the assumption that teeth are roughly pointing up along the Y axis. The output is sample points from the occlusal plane which is given to a simple principal component analysis (PCA) method to find the normal direction. SVR uses a linear loss function with a zero part within the margins which performs better for teeth dataset than the quadratic loss function in regular least square regression methods. It helps to decrease the effect of gingiva cut-lines which can be very jagged and bumpy in mesh scans. It also tries to rule out the vertical points on the teeth (buccal part) and give more weight of importance to the horizontal points on teeth (cuspal part) in determining the occusal plane orientation. The RANSAC method and Robust PCA method can alternatively be used for the alignment.

Table 1 provides exemplary pseudocode for implementing the alignment step.

TABLE 1

Pseudocode for Normal Direction Extraction

Input: a 3D mesh with a set of vertices V specified in 3D coordinate system X, Y and Z. Y represents the rough direction of vertical axis in which the teeth point upwards.
Output: the normal vector perpendicular to occlusal plane which represents the correct upward direction of teeth.
Assumptions: Teeth are roughly pointing up along the Y axis. The mesh has been truncated below the gum line.

Method steps:

1 Subtract the mean of data points to centralize the data points around (0, 0, 0).
2 Apply the Support Vector Regression with linear kernel and margin value $\epsilon$ to find the occlusal plane.
3 Find the normal direction of the occlusal plane by geometrical methods or applying a simple PCA.

Segmentation by Geometric Hill-Climbing

One of the algorithms for segmentation is based upon geometric operations on the mesh. Specifically, the main idea behind this approach is that, if one starts from any point on the surface and moves upwards through a series of points, one will converge to a high point that is a local maximum. In most cases it would be expected all points on a tooth (or on the same cusp of a tooth) will converge to the same local maximum. This type of segmentation can produce very accurate boundaries between teeth, but it typically results in an over-segmentation in which a single tooth may be divided into multiple segments.

Before performing the segmentation, the mesh is preprocessed using Laplacian smoothing. This preprocessing is an effective way of removing high-frequency noise in the surface reconstruction.

An energy function is then computed for each vertex on the mesh, on which the algorithm will attempt to find local maxima later in the hill-climbing process. The energy function at each vertex is composed of two terms, where for the i-th vertex:

$$f = y_i + \lambda d_i$$

where $y_i$ is the y-coordinate (height) of the i-th vertex, $d_i$ is its angular divergence, and $\lambda > 0$ is a weighting parameter. The parameter $\lambda$ can be any value greater than zero or, alternatively, $\lambda$ can be equal to zero.

Angular divergence is a measure of overall curvature around a point. For a face F comprised of vertices $v_i$, $v_j$, and $v_k$, with normal vectors $n_i$, $n_j$, and $n_k$, respectively, the angular divergence is given by:

$$D_F = |\cos^{-1}(n_i^T n_j)| + |\cos^{-1}(n_i^T n_k)| + |\cos^{-1}(n_j^T n_j)|$$

If the area around a face is completely flat, then all the normal vectors of all three of its vertices will point in the same direction, and the $D_F$ will be zero. Then the angular divergence of the i-th vertex $v_i$ is the mean of the angular divergences of the faces of which $v_i$ is a part.

Once the energy $f_i$ is computed for each vertex, segmentation is performed according to a hill-climbing procedure. Conceptually, the algorithm can be understood as follows. For each vertex on the surface, the algorithm initializes a hill-climb, in which at each iteration it moves to the connected neighbor (as defined by the faces) that has the highest energy function value. The algorithm continues climbing until it reaches a local maximum that has higher energy than all of its neighbors. All vertices that were passed through along this route are assigned to this local maximum, and all such paths that converge to this local maximum define a segment. This process is repeated until all vertices on the mesh have been traversed.

This segmentation assigns vertices to segments defined by local energy maxima that can be reached through a monotonically-increasing path through the energy function. The energy function $f_i$ is defined such that each iteration of hill-climbing moves upwards in height, but is discouraged from crossing an area with high curvature by the angular divergence term. This helps ensure that the boundaries between teeth are not crossed.

Figure 5:
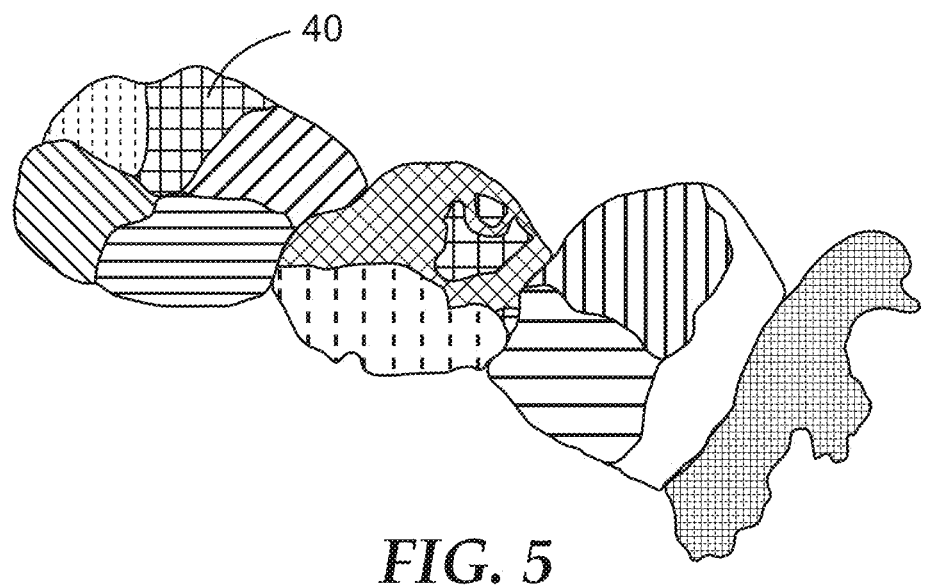
FIG. 5 illustrates over-segmentation of teeth by a geometric hill-climbing method.

An example of a segmentation produced by this algorithm is shown in FIG. 5. As can be seen, the algorithm oversegments the teeth by separating each cusp of a tooth into its own segment—this can be understood intuitively as a result of the hill-climbing procedure, since each cusp will have its own unique local maximum. For example, the digital model of tooth 40 is segmented into five sections. However, the boundaries produced by this approach are quite precise and accurately separate teeth from one another.

Table 2 provides exemplary pseudocode for implementing the geometric hill-climbing algorithm.

Segmentation by Point Classification

The segmentation by point classification is a data-driven approach. Unlike the geometric hill-climbing approach, this approach relies on manually provided groundtruth segmentation. Groundtruth can be obtained from a user providing nearly accurate segmentation manually using mesh manipulation tools such as the MeshLab system. A selection of an individual tooth can be made using a face selection tool. Individual teeth are selected in this manner and saved as individual mesh files. Using the original mesh and the individual teeth files, a labeling of the vertices in the original mesh can then be inferred. Once groundtruth for a full scan is completed, the inferred labels of all the segments can be visualized.

From this groundtruth labeling, the boundary vertices between segments can be determined. For each vertex the distribution of vertex labels around that vertex is examined. If the distribution is not unimodal (i.e., the vertex labels are predominantly the same), then that vertex is considered an interior vertex. If not, the vertex is considered a boundary vertex. This data can be manually entered one time, for example, as training data and then used repeatedly in the point classification algorithm.

Figure 6:
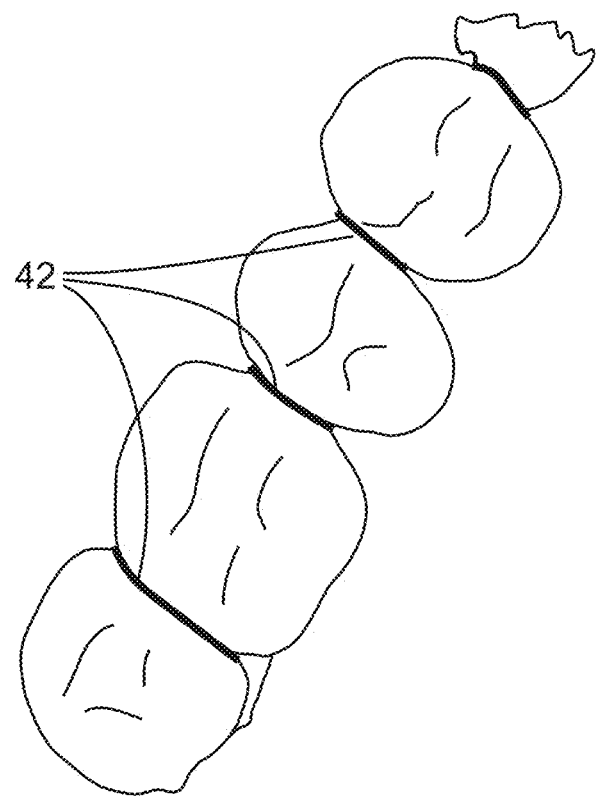
FIG. 6 illustrates detection of boundary vertices between teeth in a digital 3D model.

Given the groundtruth boundary vertices labels from multiple training meshes, the algorithm provides for a function that is capable of predicting whether a vertex on a mesh lies in the interior of a tooth or on the boundary between teeth. In particular, the algorithm can classify or label points in the mesh as being on a tooth or on a boundary between teeth. This process involves two tasks: feature extraction and classification. FIG. 6 illustrates detection of boundary vertices 42 between teeth in a digital 3D model.

Table 3 provides exemplary pseudocode for implementing the point classification (machine learning) training data algorithm.

TABLE 2

Pseudocode for Hill-Climbing Segmentation

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: Segmented mesh, where for each vertex $v_i$ in the mesh, a label $l_i$ corresponding to
the segment to which that vertex belongs is assigned.
Assumptions: Teeth are roughly pointing up along the Y axis. The mesh has been truncated below the gum line.

Method steps:

1. Perform mesh Laplacian smoothing to reduce error
2. For each vertex $v_i$ in V, compute the surface normal at that vertex
3. For each face $f_i$ in F, compute the divergence of the face as
   $D_F = |\cos^{-1}(n_i^T n_j)| + |\cos^{-1}(n_i^T n_k)| + |\cos^{-1}(n_j^T n_k)|$ where $n_i$, $n_j$ and $n_k$ are the normal directions of vertices i, j, and k of the face
4. Apply the divergence value of every face to all the individual vertices of the face
5. Compute the energy function value at each vertex as y + lambda * $D_f$
6. For each vertex determine the maximum function value in a local neighborhood
7. Assign all vertices to a segment assigned to the local maximum value in step 6
8. Repeat steps 6 to 7 until a local maximum is reached
9. Assign the appropriate cluster labels to each vertex

TABLE 3

Pseudocode for Machine Learning Training

Input: Multiple 3D meshes with a sets of vertices V specified in 3D coordinate system X, Y and Z. Y represents the vertical axis or the general direction in which the teeth point upwards. The mesh also has a set of triangulations or faces F based on the vertices. Also the groundtruth segmentation in the form of the vertices corresponding to boundaries and those in the interior as indicated by manual annotation.
Output: A predictive model that is capable of generating the boundary vertex prediction labels for a query set of vertices.
Assumptions: Teeth are roughly pointing up along the Y axis. The mesh has been truncated below the gum line.

Method steps:

1  For each vertex in every mesh in the training set of data, compute the following features:
   a. Normal direction
   b. Absolute, mean and Gaussian curvature
   c. Shape context
   d. Mesh fourier
   e. Spin image
   f. Mesh local covariance
2  Construct a data matrix X which is M X N where M is the total number of vertices in all the meshes and N is the total number of feature dimensions when all features in step
   1 are concatenated
3  Train a RUSBoosted decision tree classifier that can predict the labels corresponding to whether a vertex lies on the boundary or not. (An alternate classifier can be used.)

Feature Extraction

In order to perform this task, the point classification algorithm extracts many characteristic features for every vertex in the mesh. It is often difficult to determine which features are useful in a segmentation algorithm. There are many features which can be used for segmentation in this framework, including but not limited to multi-scale surface curvature, singular values extracted from PCA of local shape, shape diameter, distances from medial surface points, average geodesic distances, shape contexts, and spin images. Of these, the algorithm implements the following features: absolute and mean curvature, direction of normal at vertex, local covariance of the mesh around the vertex and its principal Eigen values, spin images, Fourier features, shape contexts, and PCA features.

Classification

Given the feature set for a vertex X, the function $f$ is defined as follows: $f: X \rightarrow \{1,0\}$, that is the function $f$ maps the set of features X to either a 1 or 0. A value 1 indicates that vertex is a boundary vertex and the value 0 indicates otherwise. This function can be one or a combination of many classification methods such as support vector machines, decision trees, conditional random fields, and the like. Additionally, in the segmentation as a classification problem, there is a class imbalance. The number of interior vertices is much greater than the number of boundary vertices. The ratio of interior vertices to boundary vertices is typically 100:1. In such extreme class imbalance situations, regular classifiers are not optimal. This is because it is possible to obtain very high accuracy by always predicting that a vertex is in the interior, and that would be practically useless since no vertices would be classified as being on a boundary. To remedy this issue, one option involves using classifier ensembles such as boosting.

The classification algorithm uses RUSBoosting on decision stumps as a classifier. RUSBoost stands for random undersampling boosting and is known to handle the class imbalance very well. Additionally RUSBoost is already implemented in the MATLAB program "fitensemble" function. Based on preliminary analysis, RUSBoost was performed on 700 decision stumps. This number was chosen using cross-validation on the training set with the resubstitution loss as the metric. For our experiments, we used a "leave-scan-out" cross-validation scheme. Our dataset consisted of 39 scans, and for every test scan the remaining 38 scans were used for training. The resulting predictions were compared to the groundtruth boundary labels of the test scan. A confusion matrix can then be obtained by comparing the groundtruth labels with the predicted labels. From this we obtained the false alarm rate and the hit rate. With cross-validation testing on 39 scans we obtained an 80% hit rate and 1.7% false alarm rate on average.

Table 4 provides exemplary pseudocode for implementing the point classification (machine learning) algorithm.

TABLE 4

Pseudocode for Machine Learning Prediction

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: Binarized mesh where for each vertex $v_i$ in the mesh, a label $l_i$ corresponding to whether the vertex belongs to a boundary or not.
Assumptions: Teeth are roughly pointing up along the Y axis. The mesh has been truncated below the gum line.

TABLE 4-continued

Pseudocode for Machine Learning Prediction

Method steps:

1 For each vertex $v_i$ in V, compute the following features:
   a. Normal direction
   b. Absolute, mean and Gaussian curvature
   c. Shape context
   d. Mesh fourier
   e. Spin image
   f. Mesh local covariance
2 Construct a data matrix X which is M X N where M is the number of vertices in the mesh and N is the total number of feature dimensions when all features in step 1 are concatenated
3 Predict using the learned decision tree RUSBoost classifier the labels corresponding to whether a vertex lies on the boundary or not Segmentation by Interstice Detection As an alternative to point classification, the second algorithm for segmentation can use interstice detection (step 29 in method 22). Table 5 provides exemplary pseudocode for implementing the interstice detection algorithm.

TABLE 5

Pseudocode for Interstice Detection

Input: a 3D mesh with a set of vertices V specified in 3D coordinate system X, Y and Z. Y represents the vertical axis or the general direction in which the teeth point upwards. The mesh also has a set of triangulations or faces F based on the vertices.
Output: a set of planes that approximate the intersticial spaces between each pair of teeth.
Assumptions: Teeth are roughly pointing up along the Y axis.

Method steps:

1 Form a plan-view range image of the mesh. That is, a range image from the top view, where each pixel represents the height of the surface at the corresponding point.
2 Estimate a one-dimensional parameterization of the dental arch using the Locally-Linear Embedding (LLE) algorithm, which results in a curve that represents the general shape of the arch and passes roughly through the centers of the teeth.
3 Compute a set of evenly-spaced sample points along the one-dimensional parameterization.
4 For each sample point along the curve, compute the sum of heights in the range image along a line normal to the curve at that point.
5 Intersticial spaces are identified as sample points that are local minima in the sum of heights computed in step 4. The orientation of the intersticial space is given by the direction of the normal to the one-dimensional parameterization curve at the corresponding sample point.
6 Detected intersticial spaces, and their orientations, are mapped back to the three-dimensional coordinates of the original mesh.

Morphological Clean Up

Figure 7A:
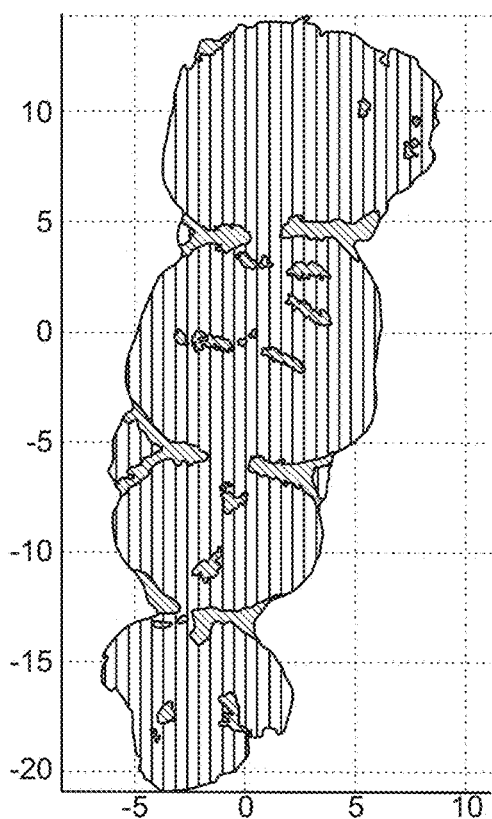
FIGS. 7A and 7B illustrate morphological clean up to fix boundaries between teeth in a digital 3D model.
Figure 7B:
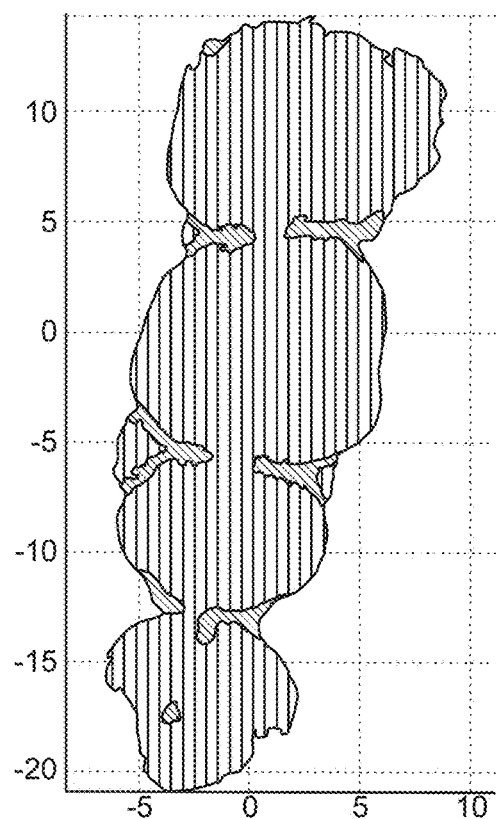

Morphological operations such as mesh erosion and dilation can be done in tandem, resulting in an operation known as morphological opening. Unlike images, mesh erosion and dilation are non-trivial since there are no sliding windows. Instead to perform mesh erosion, one can use the connected v-ring of every vertex as its neighborhood. Performing morphological opening removes islands and small streaks which can interfere with the merging algorithm mentioned later. FIGS. 7A and 7B illustrate morphological clean up to fix boundaries between teeth in a digital 3D model with FIG. 7B illustrating clean up of the boundaries shown in FIG. 7A. This morphological clean up can be used to for the optional step 32 in method 22 after the segmentation by point classification.

Complementary Approaches to Segmentation

Based on the results of the hill-climbing approach and the classification approach, it was observed that the hill-climbing captures the general geometry of cusp and has a tendency to form good boundaries around teeth, but it over-segments and thus creates more false boundaries. The classification approach on the contrary has a somewhat less than desired hit rate on boundaries but has a very low false alarm rate. From this complementary result, a method to merge the results helps reduce the demerits of both approaches and boost the merits of both. In order to accomplish this, a hierarchical merging algorithm is used, which merges the segments in the hill-climbing approach using the boundary predictions of the classification approach. Every boundary predicted by the hill-climbing approach is given a score based on the predicted boundary vertices from the classification approach. Then a hierarchical merging is performed. All the boundaries with a score less than a threshold are discarded and the corresponding segments are merged and the boundary scores are corrected accordingly. This threshold is gradually increased. For example, all boundaries that have score less than 5 are discarded first. The corresponding segments are merged, and then this process is repeated by increasing the threshold step-by-step to, for example, 50. This heuristic provides correct segmentation of the teeth in one of the merge steps in most cases.

Elimination of Non-Aligned Boundaries

Figure 8A:
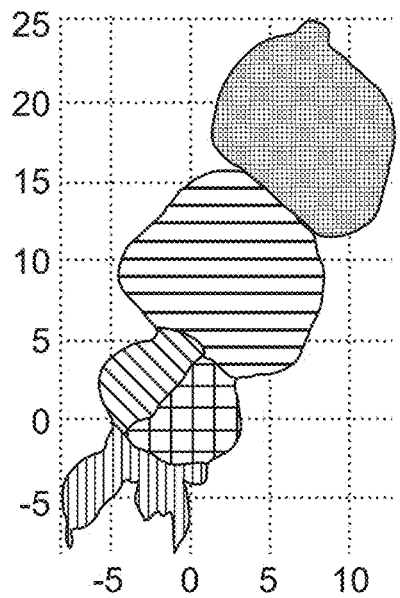
FIGS. 8A and 8B illustrate removal of non-aligned boundaries in digital 3D model.
Figure 8B:
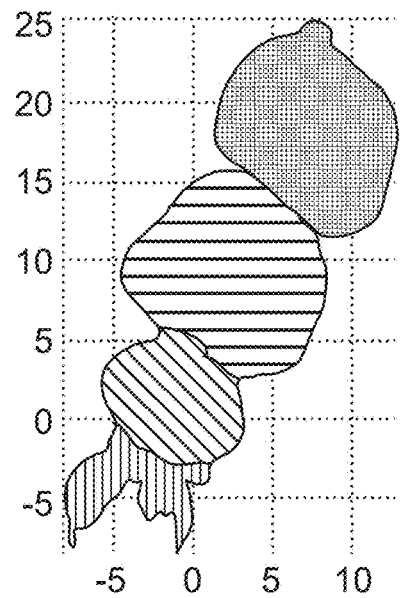

Even after the merging process, there are some strong false boundaries predicted by the machine learning classifier which are not eliminated completely. These boundaries can be removed using a hypothesis of boundary direction alignment. Since each consecutive tooth boundary is roughly parallel, there cannot be any stark changes in the boundary direction between consecutive teeth. In FIGS. 8A and 8B, a misaligned boundary is removed using such a hypothesis where FIG. 8B illustrates removal of a boundary from the model of FIG. 8A. This can be achieved by determining the principal direction of orientation of each boundary segment using PCA. The principal components (PCs) of each consecutive tooth boundary should be aligned, thus resulting in eliminating the boundaries which have misaligned PCs. This process is applied after merging the hill climbing result with the machine learning result.

Segmentation Results

Sample results of the classification or machine learning (ML), hill-climbing (HC), and the merging steps are shown in FIGS. 9A-9H. The machine learning output (FIG. 9A) shows the mesh labeling for the boundary vertices and the interior vertices. The second mesh (FIG. 9B) is the result of the hill climbing. As shown in FIG. 9B, the hill-climbing over-segments each tooth but in general there is a reduced chance of a segment being shared across teeth. This is also a behavior associated with the choice of the parameter λ. The meshes displayed in FIGS. 9C-9H indicate iteratively the result of each merge step. Merge 1 corresponds to discarding boundaries with a score less than 5 and merge 2 corresponds to scores less than 10 and so on. In this example, the correct segmentation was achieved at step 6. As shown in the example of FIGS. 9C-9H, it is possible there are no changes between some of the successive (iterative) merge steps. Successive merge steps indicate how aggressively nearby segments are merged and, therefore, in some cases changes are only noticeable at later merge steps.

The score used for merging can represent, for example, the number of points classified as a boundary from the point classification algorithm within a particular vicinity of a boundary determined from the hill-climbing algorithm. An exemplary score of 5 means at least 5 points classified as a boundary are within a particular vicinity of a boundary determined by the hill-climbing algorithm. The particular vicinity used can be based upon, for example, empirical evidence, the typical width or size of a true boundary, or other factors.

In some cases, the best result would be achieved earlier than the 6th merging step and it is possible to get an over-merged result at step 6. In this case one could use the result at step 5 manually or attempt to separate manually just the teeth that are over-merged. Sometimes, an under-merged or over-segmented result can occur even after step 6. In this scenario, by using a cursor control device and user interface a user could manually select ("click on") and merge the segments that require merging to extract the teeth correctly, for example. The final segmented digital 3D model can then be stored in an electronic storage device for later processing.

Table 6 provides exemplary pseudocode for implementing the algorithm for merging hill-climbing segmentation with point classification (machine learning) segmentation. For the alternative intestice detection segmentation, Table 7 provides exemplary pseudocode for implementing the algorithm for merging hill-climbing segmentation with interstice detection segmentation.

TABLE 6

Pseudocode for Merging Hill-Climbing and Machine Learning Prediction

Input: a 3D mesh with a set of vertices V specified in 3D coordinate system X, Y and Z. Y represents the vertical axis or the general direction in which the teeth point upwards. The mesh also has a set of triangulations or faces F based on the vertices. Label assignments from hill climbing and boundary vertex labels predicted by the machine learning are also provided.
Output: Segmented mesh, where for each vertex $v_i$ in the mesh, a label $l_i$ corresponding to the segment to which that vertex belongs is assigned.
Assumptions: Teeth are roughly pointing up along the Y axis. The mesh has been truncated below the gum line.

Method steps:

1. Convert hill-climbing label assignments to boundaries between segments and interior vertices of segments resulting in a set of boundaries B
2. Eliminate small boundary prediction regions in the machine learning prediction by way of morphological erosion. Also eliminate boundaries which are misaligned with the general orientation of the quadrant/arch
3. Initialize merge threshold to Th
4. For each boundary $b_i$ in B, compute the score of the boundary by determining the number of machine learning predicted boundary vertices in the immediate neighborhood of the boundary. Normalize this number by the length of the boundary (total number of vertices)
5. Eliminate the boundaries which have a score less than Th and merge the segments appropriately by eliminating some cluster assignments and copying cluster assignments.
6. Recompute the boundary scores according to step 4
7. Increase Th by a predetermined
8. Repeat steps 5 to 7, 5 more times
9. Assign new cluster labels to vertices

TABLE 7

Pseudocode for Merging Hill-Climbing Segments using Interstice Detection

Input: a 3D mesh with a set of vertices V specified in 3D coordinate system X, Y and Z. Y represents the vertical axis or the general direction in which the teeth point upwards. The mesh also has a set of triangulations or faces F based on the vertices. Label assignments from hill climbing, as well as detected intersticial spaces, are also provided.

TABLE 7-continued

Pseudocode for Merging Hill-Climbing Segments using Interstice Detection

Output: Segmented mesh, where for each vertex $v_i$ in the mesh, a label $l_i$ corresponding to the segment to which that vertex belongs is assigned.
Assumptions: Teeth are roughly pointing up along the Y axis.

Method steps:

1. Each detected intersticial space defines a plane in the 3D space of the mesh. For each segment found in Hill-Climbing, compute which side of each interstice plane the majority of its vertices reside. This is referred to the "polarity" of each segment with respect to each intersticial plane.
2. Merge together segments that have the same polarities with respect to nearby intersticial planes.

As an alternative to point classification and interstice detection, the algorithm can merge the hill-climbing segmentation with user input identifying centroids of teeth (step 31 in method 22). This segmentation method requires input from a user at the beginning of the process. In particular, the user identifies the centroid of each tooth in the digital 3D model of teeth. For example, when viewing the digital 3D model of teeth, such as viewing the model in FIG. 2, on display device 16, the user can use input device 18, such as a cursor control device, to select ("click on") the centroid of each tooth in the model or otherwise identify the centroid. The centroid can include the actual centroid or an estimation of the centroid as perceived by the user. This user entered information is used as the initialization for the step of the segmentation which merges the hill-climbing segments using the Kmeans method. These user-identified centroids need to be close to actual centroids of the teeth in order for the segmentation process to work well and not require post-processing by the user. The only parameter required for this method to be trained is $\epsilon$ in SVR for normal direction extraction described above for the alignment process.

The user-entered information to identify the centroids of each tooth is then merged with the results of the hill-climbing segmentation using the Kmeans clustering method. The vertices should first be replaced by the corresponding local maximum from the hill-climbing step. Then Kmeans method is applied on the new set of vertices to cluster them in k segments, where k is equal to the number of inputs ("clicks") of the user at the beginning of the process. The user's inputs (estimation of teeth centroids) are used as the centroid starting locations of the Kmeans method.

This merging method can result in successful segmentation as follows: clustering is applied on the local maxima (mostly located on the teeth cusps) and not the full mesh, yielding accuracy and speed benefits. The local maxima of larger clusters find higher weights in Kmeans method, and the centroid starting locations entered by the user avoid converging to other possible local optima of Kmeans methods.

Table 8 provides exemplary pseudocode for implementing the algorithm for merging hill-climbing segmentation with user-entered estimations of teeth centroids.

TABLE 8

Pseudocode for Merging Hill-Climbing Segments using Kmeans

Input: a 3D mesh with a set of vertices V specified in 3D coordinate system X, Y and Z, the segmentation result from the hill-climbing segmentation algorithm, in which the local maximum coordination that has been reached by each vertex is reported, and the estimation of centroids of teeth, which has been received from the user at the beginning of the process.
Output: Segmented mesh, where to each vertex $v_i$ in the mesh, a label $l_i$ corresponding to the segment to which that vertex belongs is assigned.

Method steps:

1. Represent/substitute each vertex with the local maximum it has reached.
2. Apply the Kmeans clustering method on the new vertices, with the user's centroid estimation as the centroid starting locations of the Kmeans.
3. Assign all vertices to a segment assigned to the corresponding local maximum value in step 2.
4. Assign the appropriate cluster labels to each vertex.

The exemplary pseudocode in Tables 1-8 is provided for illustrative purposes of particular implementations of the described algorithms, and other implementations are possible.

Tooth Wear Assessment

The assessment is a technique for detecting and analyzing tooth wear in sequential intra-oral 3D scans. Sequential means that at least two scans have been acquired for a given patient at different points in time. The changes between these two scans are assessed in order to locate areas where significant wear or erosion has occurred. Before this assessment is performed, the teeth have already been segmented from one another in the corresponding digital 3D model, and the corresponding teeth at times 1 and 2 have been registered (i.e., aligned as closely as possible in a common coordinate system). The areas of change, where significant tooth wear has occurred, are defined as worn areas.

Figure 10:
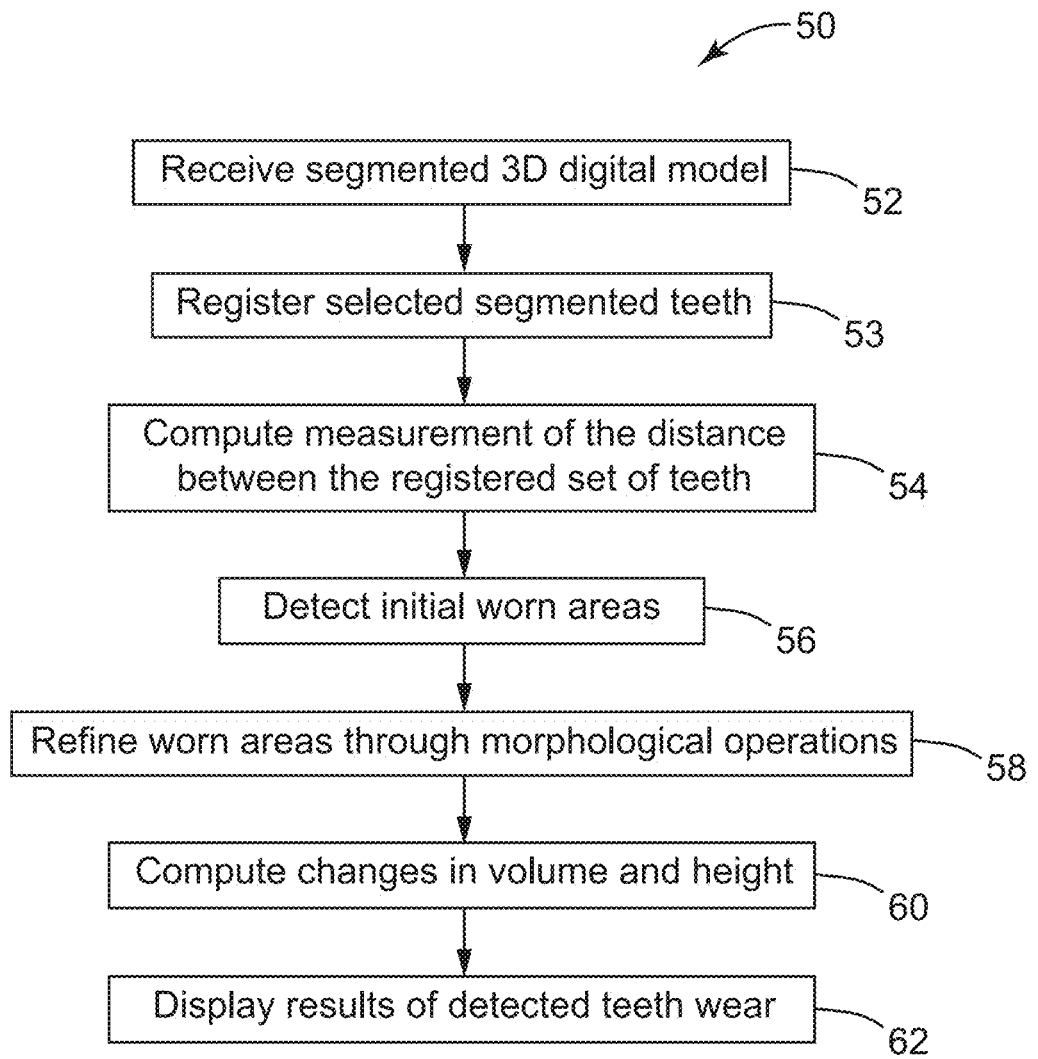
FIG. 10 is a flow chart of a method for detecting and displaying tooth wear using intra-oral 3D models.

FIG. 10 is a flow chart of a method 50 for detecting and displaying tooth wear using intra-oral 3D models. Method 50 can be implemented in software or firmware modules, for example, for execution by processor 20. Method 50 can alternatively be implemented in hardware modules or a combination of software and hardware.

Method 50 includes receiving a segmented and registered 3D model of a patient's teeth (step 52), which can be provided by, for example, the results of method 22, and registering selected segmented teeth (step 53). The registration involves obtaining segmented 3D models of a tooth from scanning the tooth at two different times, and rotating and translating the models to align them together for use in detecting changes in the two models. The rotation and translation for registration can involve aligning the two models to a common coordinate system to arrange them with the same orientation for comparison. In particular, registration is the process of aligning or obtaining the best fit rotation and translation that needs to be applied to a moving mesh to align with the fixed mesh or generalized to multiple meshes.

In an exemplary embodiment, the registration (step 53) can use the iterative closest point (ICP) algorithm to achieve registration between meshes representing the digital 3D models. One variant of the ICP algorithm includes the steps in Table 9. For the exemplary embodiment, the registration (with reference to the steps in Table 9) uses all points in step 1, Euclidean and point to plane in step 2, equal weights of pairs and rejecting them based on a fixed predetermined threshold (steps 3 and 4), sum of squared distances as the metric in step 5, and minimization is achieved in step 6 using singular value decomposition (SVD) and levenberg marquart methods.

Optionally, once a final registration optimum has been reached, one could verify that this is indeed a stable optimum. This can be done in two possible ways—first, by perturbing the optimum by small amounts of rotation and translation to determine if it converges back to the original optimum or whether a better optimum can be reached; second, by performing random restarts of the ICP algorithm with varying amounts of initial rotation and translation to determine the best optimum among those reached for each initialization.

and 2 (step 54); detect initial worn areas by finding vertices that have moved significantly in the negative direction, for example moved inwards (step 56); refine worn areas through morphological operations (step 58); and compute changes in volume and height (step 60). Each of these steps is described in more detail below. The results of detected tooth wear can then be displayed (step 62), for example on display device 16.

Step 54—Compute a Measurement of the Distance Between the Registered Set of Teeth The 3D surfaces are represented as triangular meshes, which are composed of vertices (points in 3D space) and faces which define the connections between neighboring vertices. Given two meshes representing the same tooth at times 1 and 2, and with these two meshes having already been registered, this assessment measures if and how each vertex has moved between these two scans. It is not necessary to find a perfect 1-to-1 correspondence for each vertex between the two meshes, since the shape of the tooth may have changed, and also the sampling of the surface represented by the vertices will in general change in subsequent scans. As such, the assessment approximates this measurement by finding the approximate correspondence for each vertex in its normal direction. The normal vector for each vertex and face can be computed. Then, for each vertex, the assessment searches for points along or near the normal vector (in either the positive or negative direction). The closest such point is considered the best match for this vertex, and the distance that this vertex is said to have displaced is given by the distance between the two points, projected onto the normal vector.

Figure 11:
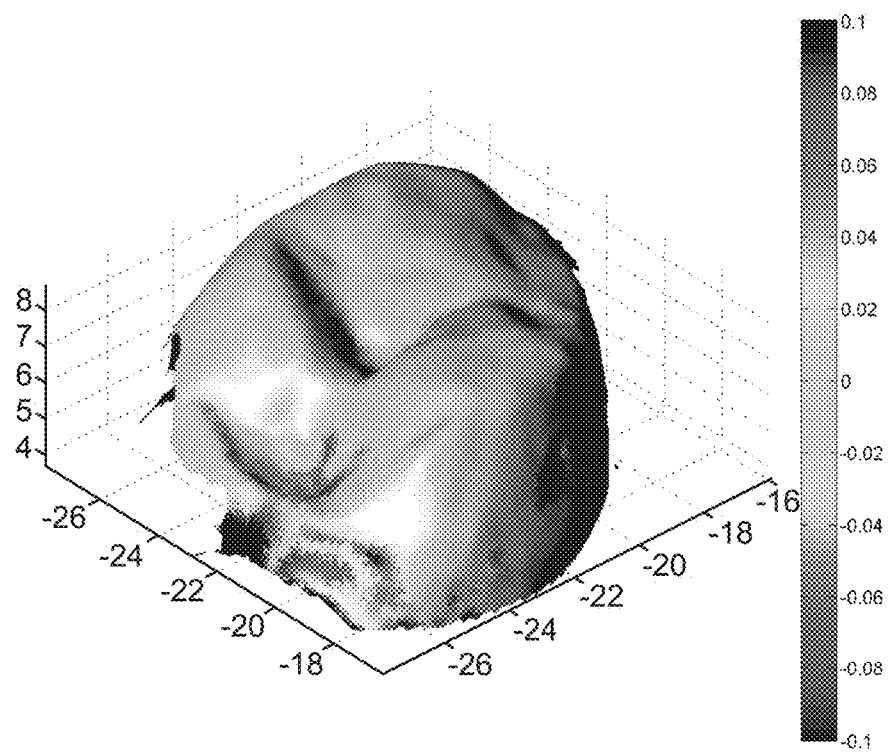
FIG. 11 is a heat map of a tooth representing displacements between first and second times.

Once this has been computed for each vertex, it is possible to display a heat map of displacement, where the color of each vertex represents how far it has moved between times 1 and 2. The sign of the displacement corresponds to the direction it has moved along its normal vector. An example of such a heat map is shown in FIG. 11. The shading in the heat map can indicate change (or displacements) between the scans of the tooth between times 1 and 2. Different colors

TABLE 9

ICP Algorithm Steps

1 Selection of points in the meshes to be registered. There are a few ways to select these points:
  a. Select all points
  b. Select a random subsample
  c. Uniformly subsample
  d. Select points corresponding to key features such as curvature and local covariance
2 Finding matching (corresponding) points is the step in which the closest point in the second mesh for every point in the first mesh is determined using a suitable distance metric. This step can also be achieved using different metrics:
  a. Euclidean point to point distance
  b. Point to plane distance or distance along normal
  c. Reverse calibration
  d. Other combinations
3 Weighting of pairs corresponds to ranking the correspondences. This can be done using some weights based on distances, weights based on normal direction compatibility, or other factors.
4 Rejecting pairs can be done using thresholds on the weights computed in the previous step among other heuristics.
5 Error metric for optimization can be calculated as the sum of the squared distances between the pairs remaining after step 4. The distances can also be point to plane distance as in step 2.
6 Optimization can be done using SVD (singular value decomposition), levenberg marquart optimization, BFGS, stochastic gradient descent, simulated annealing, or other techniques.

The approach for detecting and analyzing worn areas includes the following steps: compute a measurement of the distance between the registered set of teeth between times 1 can also be used to indicate the extent or severity of the changes. The changes can be shown individually for each tooth or for all scanned teeth as an arch.

Step 56—Detect Initial Worn Areas

Figure 12:
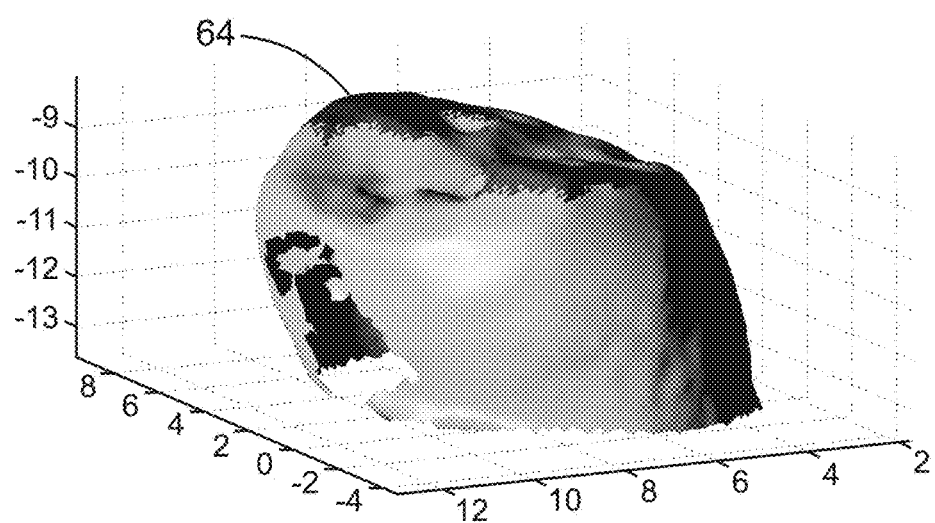
FIG. 12 illustrates detection of initial wear areas on a digital 3D model of teeth.

Once the displacements have been approximated, the next step is to compute initial estimates of where potential worn areas might be located. Since tooth wear is a subtractive process, the assessment determines areas in the comparison of the models from times 1 and 2 where a negative displacement has been measured. Initial worn areas are detected by locating vertices where the change, in the negative direction, is over a particular threshold. An example is shown in FIG. 12 illustrating a worn area 64 on a digital model of a tooth. The bite contact points between teeth can also be used for detection of initial worn areas.

Step 58—Refine Worn Areas Through Morphological Operations

In some cases the initial worn areas detected in step 56 may be subject to noise and other irregularities in the meshes. As such, using these initial worn areas as a starting point, the next step is to refine them using morphological operations on the mesh.

For these operations, the mesh is treated similar to a binary image, with vertices in the initial worn areas having a value of one, and all other having a value of zero, and with the faces defining the connections between vertices. The first step is to perform an erosion, which results in a slight shrinkage in the worn areas. This step serves to remove small isolated worn areas, such as a single point in the mesh or a small enough collection of points to be deemed noise, and to refine the remaining worn areas so that they are more smooth.

Next, a region growing operation is iteratively performed. At each iteration, new points are added to the worn areas if they are adjacent to current worn areas and have a negative displacement that is larger than a particular threshold (which is smaller than the threshold used to detect the initial worn areas in step 56). These points added to the mesh provide for a more complete worn area.

Figure 13:
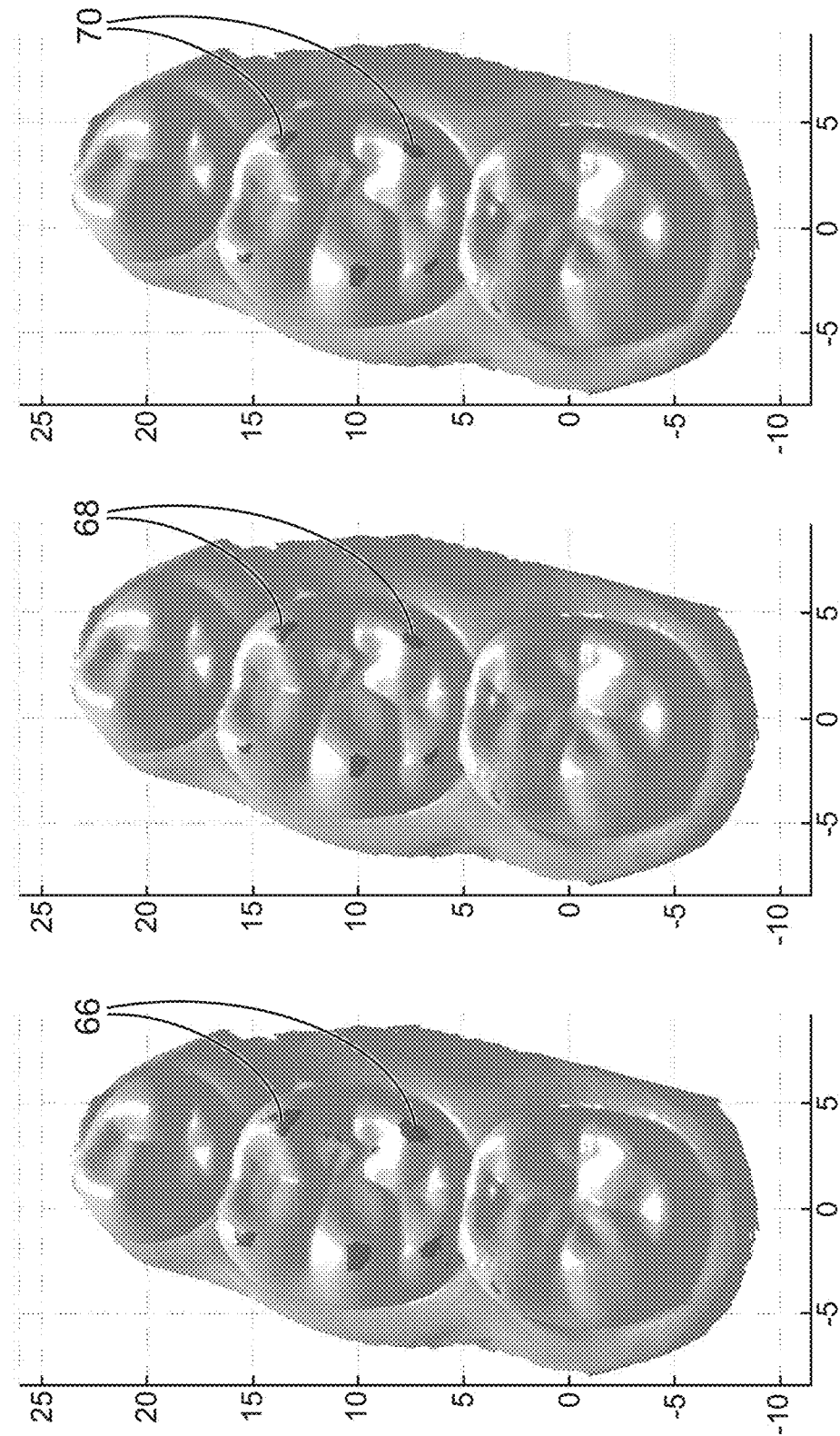
FIGS. 13A-13C illustrate morphological operations on wear areas on a digital 3D model of teeth.

An example of this procedure is illustrated in FIGS. 13A-13C illustrating iterative processing of worn areas represented by the darker shading, such as areas 66, 68, and 70. In particular for this example, FIG. 13A shows initial worn areas, FIG. 13B shows the worn areas after an erosion processing to remove points, and FIG. 13C shows the worn areas after a region growing processing to add points.

Step 60—Compute Changes in Volume and Height

Once the worn areas have been finalized, the quantitative changes in volume and height in the tooth between times 1 and 2 can be computed. These measurements can be useful as diagnostic aides for assessing tooth wear and Bruxism.

Changes in volume are computed by integrating the volumes between the surfaces of the models at times 1 and 2 within all the vertices deemed worn areas in the previous steps. Changes in height are measured per cusp in the models (since some teeth, such as molars, have multiple cusps). In each cusp worn area, the point with largest change is located and designate as the height of change in this worn area.

Alternatively, the volume can be computed using the following approach.

For tooth at time 1: slice with a horizontal plane (parallel to XZ plane) at a certain value of Y, above which the changes should be. Measure volume above this plane by summation of volumes in the vertical direction along the plane using a parameterization by (x,z) coordinates of a regular grid on the plane.

For tooth at time 2: repeat the step to measure volume.

Then: subtract the first volume from the second one to obtain a volume difference measurement.

Figure 14:
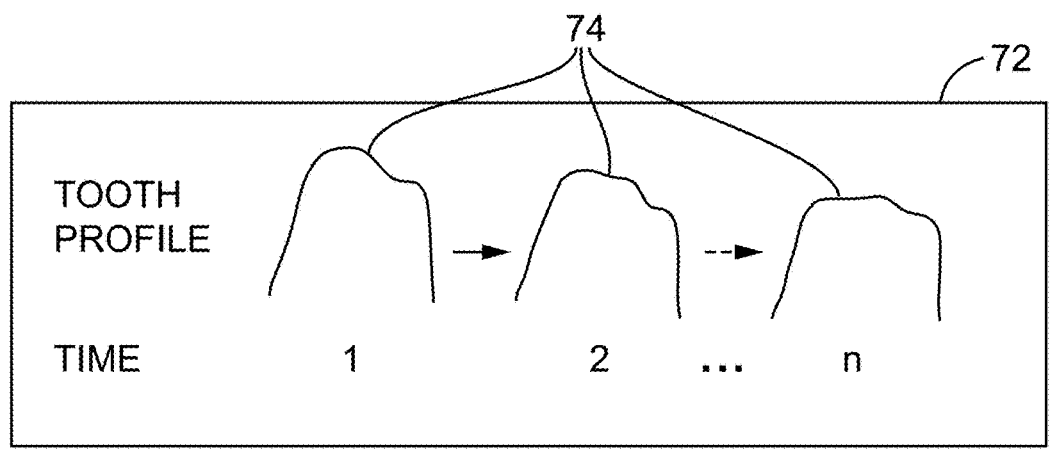
FIG. 14 is a diagram of a user interface for illustrating tooth wear.

FIG. 14 is a diagram of a user interface 72 illustrating tooth wear. User interface 72 can be displayed on display device 16, for example, and includes a digital tooth profile illustrating wear on area 74 over time. The tooth profile can be generated from the segmented 3D model of teeth. The change in volume and height based upon wear on area 74 can be calculated. The volume lost in a particular tooth can also be shown in other ways such as a graph of changes in tooth height or volume, or an animation showing change in the tooth over time.

The invention claimed is:

1. A method for detecting tooth wear, comprising steps of:
receiving first and second digital 3D models of teeth, wherein the first digital 3D model was taken a first time, and the second digital 3D model was taken at a second time later than the first time;
segmenting the first digital 3D model of teeth to digitally separate individual tooth within the first digital 3D model of teeth and generate a segmented first digital 3D model of teeth, comprising:
performing a first segmentation method for the first digital 3D model of teeth; and
performing a second segmentation method, different from the first segmentation method, for the first digital 3D model of teeth;
repeating the segmenting step for the second digital 3D model of teeth to digitally separate individual tooth within the second digital 3D model of teeth and generate a segmented second digital 3D model of teeth; and
comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting step comprises:
performing the first segmentation method that over segments at least some of the teeth within the first digital 3D model of teeth and outputs as results the first digital 3D model of teeth with the over segmentation;
performing the second segmentation method that classifies some points within the first digital 3D model of teeth as being on an interior of a tooth in the first digital 3D model of teeth and classifies some other points within the first digital 3D model of teeth as being on a boundary between teeth in the first digital 3D model of teeth and outputs as results the first digital 3D model of teeth with the classification; and
combining the results of the first and second segmentation methods to generate the segmented first digital 3D model of teeth.

2. The method of claim 1, further comprising registering a tooth in the segmented first digital 3D model of teeth with the same tooth in the segmented second digital 3D model of teeth in order to align a first segmented model of the tooth with a second segmented model of the same tooth.

3. The method of claim 2, wherein the comparing step comprises determining a measurement of a distance between the tooth in the segmented first digital 3D model of teeth and the same tooth in the segmented second digital 3D model of teeth.

4. The method of claim 1, wherein the combining step comprises iteratively combining the results of the first and second segmentation methods.

5. The method of claim 1, wherein the segmenting step further comprises detecting non-aligned boundaries in the segmented first digital 3D model of teeth and removing the non-aligned boundaries.

6. The method of claim 1, wherein the segmenting step further comprises refining the segmented first digital 3D model of teeth based upon user input.

7. The method of claim 1, wherein the comparing step comprises displaying a digital 3D model of one or more of the teeth with a visual indication of worn areas.

8. The method of claim 7, wherein the displaying further comprises displaying an animation of the visual indication of the worn areas.

9. The method of claim 2, wherein the registering step comprises:
selecting a first plurality of points for the tooth in the segmented first digital 3D model of teeth and a second plurality of points for the tooth in the segmented second digital 3D model of teeth; and
matching points in the first plurality of points with closest corresponding points in the second plurality of points using a distance metric.

10. A method for detecting tooth wear, comprising steps of:
receiving first and second digital 3D models of teeth, wherein the first digital 3D model was taken a first time, and the second digital 3D model was taken at a second time later than the first time;
segmenting the first digital 3D model of teeth to digitally separate individual tooth within the first digital 3D model of teeth and generate a segmented first digital 3D model of teeth, comprising:
performing a first segmentation method for the first digital 3D model of teeth; and
performing a second segmentation method, different from the first segmentation method, for the first digital 3D model of teeth;
repeating the segmenting step for the second digital 3D model of teeth to digitally separate individual tooth within the second digital 3D model of teeth and generate a segmented second digital 3D model of teeth; and
comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting step comprises:
performing the first segmentation method that over segments at least some of the teeth within the first digital 3D model of teeth and outputs as results the first digital 3D model of teeth with the over segmentation;
performing the second segmentation method that approximates intersticial spaces between each pair of teeth within the first digital 3D model of teeth and outputs as results the first digital 3D model of teeth with the approximation of the intersticial spaces; and
combining the results of the first and second segmentation methods to generate the segmented first digital 3D model of teeth.

11. A method for detecting tooth wear, comprising steps of:
receiving first and second digital 3D models of teeth, wherein the first digital 3D model was taken a first time, and the second digital 3D model was taken at a second time later than the first time;
segmenting the first digital 3D model of teeth to digitally separate individual tooth within the first digital 3D model of teeth and generate a segmented first digital 3D model of teeth, comprising:
performing a first segmentation method for the first digital 3D model of teeth; and
performing a second segmentation method, different from the first segmentation method, for the first digital 3D model of teeth;
repeating the segmenting step for the second digital 3D model of teeth to digitally separate individual tooth within the second digital 3D model of teeth and generate a segmented second digital 3D model of teeth; and
comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting step comprises:
performing the first segmentation method that over segments at least some of the teeth within the first digital 3D model of teeth and outputs as results the first digital 3D model of teeth with the over segmentation;
performing the second segmentation method that receives user-entered estimations of centroids of teeth in the first digital 3D model of teeth and outputs as results the first digital 3D model of teeth with the user-entered estimations of the centroids; and
combining the results of the first and second segmentation methods to generate the segmented first digital 3D model of teeth.

12. A system for detecting tooth wear, comprising:
a module for receiving first and second digital 3D models of teeth, wherein the first digital 3D model was taken a first time, and the second digital 3D model was taken at a second time later than the first time;
a module for segmenting the first digital 3D model of teeth to digitally separate individual tooth within the first digital 3D model of teeth and generate a segmented first digital 3D model of teeth, comprising:
a module for performing a first segmentation method for the first digital 3D model of teeth; and
a module for performing a second segmentation method, different from the first segmentation method, for the first digital 3D model of teeth;
a module for repeating the segmenting for the second digital 3D model of teeth to digitally separate individual tooth within the second digital 3D model of teeth and generate a segmented second digital 3D model of teeth; and
a module for comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting module comprises:
a module for performing the first segmentation method that over segments at least some of the teeth within the first digital 3D model of teeth and outputs as results the first digital 3D model of teeth with the over segmentation;
a module for performing the second segmentation method that classifies some points within the first digital 3D model of teeth as being on an interior of a tooth in the first digital 3D model of teeth and classifies some other points within the first digital 3D model of teeth as being on a boundary between teeth in the first digital 3D model of teeth and outputs as results the first digital 3D model of teeth with the classification; and a module for combining the results of the first and second segmentation methods to generate the segmented first digital 3D model of teeth.

13. The system of claim 12, further comprising a module for registering a tooth in the segmented first digital 3D model of teeth with the same tooth in the segmented second digital 3D model of teeth in order to align a first segmented model of the tooth with a second segmented model of the same tooth.

14. The system of claim 13, wherein the comparing module comprises a module for determining a measurement of a distance between the tooth in the segmented first digital 3D model of teeth and the same tooth in the segmented second digital 3D model of teeth.

15. The system of claim 12, wherein the combining module comprises a module for iteratively combining the results of the first and second segmentation methods.

16. The system of claim 12, wherein the segmenting module further comprises a module for detecting non-aligned boundaries in the segmented first digital 3D model of teeth and removing the non-aligned boundaries.

17. The system of claim 12, wherein the segmenting module further comprises a module for refining the segmented first digital 3D model of teeth based upon user input.

18. The system of claim 12, wherein the comparing module comprises a module for displaying a digital 3D model of one or more of the teeth with a visual indication of worn areas.

19. The system of claim 18, wherein the module for displaying further comprises a module for displaying an animation of the visual indication of the worn areas.

20. A system for detecting tooth wear, comprising:
a module for receiving first and second digital 3D models of teeth, wherein the first digital 3D model was taken a first time, and the second digital 3D model was taken at a second time later than the first time;
a module for segmenting the first digital 3D model of teeth to digitally separate individual tooth within the first digital 3D model of teeth and generate a segmented first digital 3D model of teeth, comprising:
 a module for performing a first segmentation method for the first digital 3D model of teeth; and
 a module for performing a second segmentation method, different from the first segmentation method, for the first digital 3D model of teeth;
a module for repeating the segmenting for the second digital 3D model of teeth to digitally separate individual tooth within the second digital 3D model of teeth and generate a segmented second digital 3D model of teeth; and
a module for comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting module comprises:
a module for performing the first segmentation method that over segments at least some of the teeth within the first digital 3D model of teeth and outputs as results the first digital 3D model of teeth with the over segmentation;
a module for performing the second segmentation method that approximates intersticial spaces between each pair of teeth within the first digital 3D model of teeth and outputs as results the first digital 3D model of teeth with the approximation of the intersticial spaces; and
a module for combining the results of the first and second segmentation methods to generate the segmented first digital 3D model of teeth.

21. A system for detecting tooth wear, comprising:
a module for receiving first and second digital 3D models of teeth, wherein the first digital 3D model was taken a first time, and the second digital 3D model was taken at a second time later than the first time;
a module for segmenting the first digital 3D model of teeth to digitally separate individual tooth within the first digital 3D model of teeth and generate a segmented first digital 3D model of teeth, comprising:
 a module for performing a first segmentation method for the first digital 3D model of teeth; and
 a module for performing a second segmentation method, different from the first segmentation method, for the first digital 3D model of teeth;
a module for repeating the segmenting for the second digital 3D model of teeth to digitally separate individual tooth within the second digital 3D model of teeth and generate a segmented second digital 3D model of teeth; and
a module for comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth,
wherein the segmenting module comprises:
a module for performing the first segmentation method that over segments at least some of the teeth within the first digital 3D model of teeth and outputs as results the first digital 3D model of teeth with the over segmentation;
a module for performing the second segmentation method that receives user-entered estimations of centroids of teeth in the first digital 3D model of teeth and outputs as results the first digital 3D model of teeth with the user-entered estimations of the centroids; and
a module for combining the results of the first and second segmentation methods to generate the segmented first digital 3D model of teeth.

22. A method for detecting tooth wear, comprising steps of:
receiving first and second digital 3D models of teeth, wherein the first digital 3D model was taken a first time, and the second digital 3D model was taken at a second time later than the first time;
segmenting the first digital 3D model of teeth to digitally separate individual tooth within the first digital 3D model of teeth and generate a segmented first digital 3D model of teeth;
repeating the segmenting step for the second digital 3D model of teeth to digitally separate individual tooth within the second digital 3D model of teeth and generate a segmented second digital 3D model of teeth; and comparing the segmented first digital 3D model of teeth with the segmented second digital 3D model of teeth to detect tooth wear by determining differences between the segmented first digital 3D model of teeth and the segmented second digital 3D model of teeth where the differences relate to a same tooth, further comprising aligning the first and second digital 3D models of teeth, comprising:

centralizing points for the first and second digital 3D models of teeth around a particular point;

finding an occlusal plane for the centralized points; and finding a normal direction of the occlusal plane.

* * * * *